(12) United States Patent
Fusari et al.

(10) Patent No.: US 7,818,353 B2
(45) Date of Patent: *Oct. 19, 2010

(54) METHODS AND APPARATUS FOR PROCESSING A CONTEXT CHANGE REQUEST

(75) Inventors: David Fusari, Groton, MA (US); Robert Seliger, Winchester, MA (US)

(73) Assignee: Sentillion, Inc., Andover, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/606,500

(22) Filed: Oct. 27, 2009

(65) Prior Publication Data

US 2010/0114960 A1    May 6, 2010

Related U.S. Application Data

(63) Continuation of application No. 10/962,178, filed on Oct. 8, 2004, now Pat. No. 7,647,328.

(51) Int. Cl.
G06F 17/30 (2006.01)

(52) U.S. Cl. .................................. 707/803; 707/609

(58) Field of Classification Search .............. 707/609, 707/803, 999.1; 717/174
See application file for complete search history.

(56) References Cited

U.S. PATENT DOCUMENTS

| 5,734,871 | A | 3/1998 | Kleinerman et al. | |
|---|---|---|---|---|
| 7,395,215 | B2 * | 7/2008 | Grushka | 705/2 |
| 7,483,908 | B2 * | 1/2009 | Seliger et al. | 1/1 |
| 7,526,488 | B2 * | 4/2009 | Herold | 1/1 |
| 2004/0034707 | A1 * | 2/2004 | Royer | 709/227 |

FOREIGN PATENT DOCUMENTS

| WO | WO 01/16720 A2 | 3/2001 |
|---|---|---|
| WO | WO 02/48865 A2 | 6/2002 |

OTHER PUBLICATIONS

Examination Report from European Patent Application No. 04815759.8 dated Feb. 11, 2010.

\* cited by examiner

*Primary Examiner*—Cheryl Lewis
(74) *Attorney, Agent, or Firm*—Wolf, Greenfield & Sacks, P.C.

(57) ABSTRACT

A method and apparatus for use in a computer system comprising at least two software applications sharing context, wherein a context change may be requested by a user of at least one of the at least two software applications. In response to the user requesting a change from a first context to a second context, at least one business rule is applied to at least a portion of the first context and/or to at least a portion of the second context to obtain at least one result from the application of the business rule. In response to the at least one result, at least one act is performed selected from the group consisting of: denying the request to change from the first context to the second context; requesting the user to provide information relating to the requested change; and requesting the user to affirm information relating to the requested change.

80 Claims, 5 Drawing Sheets

METHODS AND APPARATUS FOR PROCESSING A CONTEXT CHANGE REQUEST

RELATED APPLICATIONS

This application is a continuation of U.S. application Ser. No. 10/962,178, U.S. Pat. No. 7,647,328, entitled "Methods And Apparatus For Processing A Context Change Request In A CCOW Environment," filed Oct. 8, 2004, bearing which is incorporated herein by reference in its entirety.

BACKGROUND OF INVENTION

The Health Insurance Portability and Accountability Act (HIPAA) protects the privacy rights of medical patients by providing guidelines and requirements for access to patient information. For example, HIPAA provides that only specific individuals may access certain information related to particular patients. Caregivers, such as primary care physicians, nurses and others, may be required by HIPAA to have a clinical affiliation with a patient in order to view the patient's information. Some clinical organizations may impose additional constraints on access to patient information.

In some clinical settings, computer systems provide users with access to information related to patients. For example, patient information such as billing, insurance and/or diagnostic information may reside in electronic file storage (e.g., one or more databases) and be accessed using one or more software applications. Some conventional software applications provide functionality which facilitates compliance with HIPAA and/or organizational policies. For example, some software applications request that a user affirm that a clinical affiliation exists between the user and the patient or specify the nature of the affiliation, before allowing the user to view the patient's information. Thus, the user is forced to make an affirmative representation that the access to patient information is in compliance with HIPAA regulations, and a record may be retained for future audits.

Some computer systems which include clinical software applications provide context management capability. As described in commonly assigned U.S. patent application Ser. No. 09/545,396, U.S. Pat. No. 6,993,556, which is incorporated herein by reference, context management capability may be provided via a context manager which can communicate with a plurality of software applications. The context manager may facilitate a sharing of context between applications, wherein the context may include information associated with a user, patient, clinical encounter or other information relevant to the application. As an example, in a system having context management capability, when a user employing a first software application to view information on a patient switches to a second software application to continue work related to that patient, the system may retain a context which automatically identifies the patient and the user to the second application, so that, for example, the user need not provide a user or patient identifier to the second application to begin work. As a result, the user need not perform the time-consuming processes of logging into the second application and providing a patient identifier to access the patient's information. As mentioned above, a context may include any information suitable for sharing between applications.

A standard known as Health Level Seven Context Management Specification was established by the Health Level Seven Clinical Context Object Workgroup (CCOW) to define a standard for an interface and components of a context management system architecture. The standard is referred to herein-after as "the CCOW standard." In accordance with the CCOW standard, a context manager facilitates a sharing of context data between applications, wherein context data provides information on various subjects, such as a user, patient, encounter, and others. When a change from one context to another is desired (e.g., when a user wishes to view information on a different patient), a context change transaction is executed, and context data related to one or more subjects may be updated to implement the context change. For example, if a user desires to change the patient for which information is viewed, then a context change transaction may update the patient subject data within a context, but leave other context data (i.e., data on other subjects) intact. For example, the user subject data may be left intact by this context change transaction, so that the user need not log into other applications again to view information on the new patient.

Some context management systems allow user access to patient information (and other information) to be audited, so that compliance with HIPAA, organizational policies and/or other standards may be monitored. For example, a context management system having audit capability is described in commonly assigned U.S. patent application Ser. No. 10/014, 341, U.S. Pat. No. 6,941,313, which is incorporated herein by reference.

FIG. 1 illustrates an exemplary computer system including a context manager with audit capability, wherein context manager 130 communicates with context-enabled applications 110 and 120 to facilitate context sharing there between. In the system of FIG. 1, applications 110 and 120 both reside on workstation 100, and both may be capable of accessing patient information. Context manager 130 communicates with a storage facility 150 that stores information provided by context manager 130, such as information related to context changes initiated by users of applications 110 and 120. Such information may include an indication of the user who initiated the context change, the patient whose information the user attempted to access, and/or the application employed by the user to initiate the change.

Auditor 140 may extract information from storage facility 150 to determine compliance with HIPAA, organizational policies, and/or other standards. For example, auditor 140 may produce reports which show the patient records that have been accessed by certain users. Auditor 140 may also be configured to produce and send an alert to an administrator if a user who is not authorized to view a particular patient's records attempts to access those records. Other monitoring and/or auditing functions may also be performed.

In certain cases, a user may not be required to have an existing clinical affiliation with a patient to be authorized to view the patient's information. For example, a clinician may need to view a patient's records in an emergency, particularly if the patient's primary caregiver is not available and the patient is in danger. This is commonly referred to in the health care industry as "break the glass" access. In general, a user may break the glass to view patient information if the user is aware that they are not otherwise authorized to access the patient's information, but must to do so to provide proper care for the patient. For example, a clinician may break the glass to determine whether an unconscious patient has any known allergies before administering medication to the patient.

SUMMARY OF INVENTION

One embodiment is directed to a method performed in a computer system comprising at least two software applications sharing context, wherein a context change may be requested by a user of at least one of the at least two software applications. The method comprises acts of: (A) in response to the user requesting a change from a first context to a second context, applying at least one business rule to at least a portion of the first context and/or to at least a portion of the second context to obtain at least one result from the application of the business rule; and (B) in response to the at least one result, performing at least one act selected from the group consisting of: denying the request to change from the first context to the second context; requesting the user to provide information relating to the requested change; and requesting the user to affirm information relating to the requested change. Another embodiment is directed to at least one computer-readable medium encoded with instructions which, when executed, perform the above-described method.

Yet another embodiment provides an agent for use in a computer system comprising at least two software applications sharing context, wherein a context change may be requested by a user of at least one of the at least two software applications. The agent comprises: at least one processor programmed to, in response to the user requesting a change from a first context to a second context; apply at least one business rule to at least a portion of the first context and/or to at least a portion of the second context to obtain at least one result from the application of the business rule; and in response to the at least one result, perform at least one act selected from the group consisting of: denying the request to change from the first context to the second context; requesting the user to provide information relating to the requested change; and requesting the user to affirm information relating to the requested change.

DETAILED DESCRIPTION

As mentioned above, HIPAA protects the privacy rights of medical patients by providing guidelines and restrictions on who may access their information, and under what circumstances. Typically, a clinician is required to have a clinical affiliation with a patient (e.g., the patient may be a patient of a healthcare organization which employs the clinician) to access the patient's records. Conventionally, systems which provide access to patient records do not prevent access by any individual, in part to protect the safety of the patient in an emergency situation. For example, in an emergency situation, a caregiver having no affiliation with the patient may wish to gain access to the patient's records to determine information that may be vital to providing care to the patient in the emergency situation (e.g., whether the patient has any allergies to certain medications, whether the patient is taking particular medications, etc.). Thus, it is generally accepted that the user should be able to "break the glass" to have access to a patient's records in an emergency situation. As a result, systems typically do not impose an absolute prohibition on access. However, in some situations (e.g., relating to the records for a public figure), an absolute prohibition on access may be imposed for unauthorized users.

Figure 1:
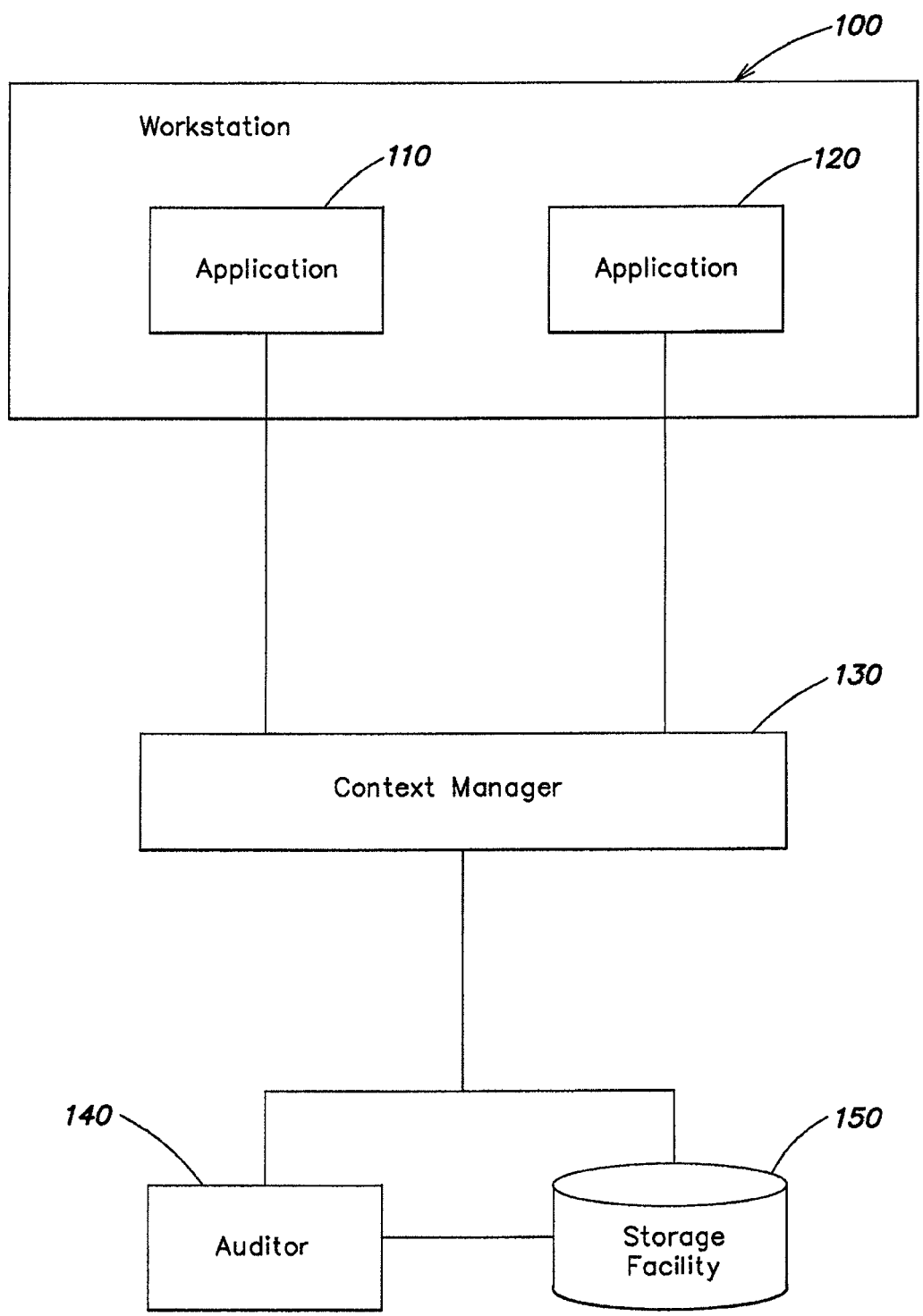
FIG. 1 is a block diagram showing a conventional context management system having audit capability.

In view of the desirability of providing break the glass access, conventional context management systems rely upon an auditor (e.g., 140 in FIG. 1) to track access to patient records by users. Specifically, user access leaves behind an audit trail that can be subsequently examined to determine compliance with HIPAA. Applicants have appreciated that while providing such an audit capability is advantageous, an improved system can be achieved by requiring users to explicitly justify their authorization to access data on particular patients. For example, in accordance with one embodiment of the present invention, a user seeking to access information for a particular patient may be called upon to justify their authorization to access that patient's records, such as by explaining the user's affiliation with the patient.

Applicants have appreciated that requesting a user to justify access to a particular patient's records can provide a number of advantages. First, requesting such a justification can reduce the likelihood of inadvertent unauthorized access, as a user will be called upon to specifically justify the basis for the access request, thereby reducing the likelihood that a user will accidentally (e.g., without considering whether or not the access is authorized) access a patient's records. Second, requesting such a justification can deter a user seeking unauthorized access, as the user will be called upon to justify the access, such that if the user wishes to continue, they will be forced to make an affirmative misrepresentation. Concerns about explaining such an affirmative misrepresentation in the event of an audit can provide a significant deterrent effect. Third, the nature of certain justifications can be used as a basis for triggering various levels of audit review. For example, if a user were to justify access by stating that it took place during an emergency break the glass scenario, such a justification can be highlighted by an auditing capability, so that the access request can be investigated to determine whether an emergency situation truly existed that justified the break the glass access.

One embodiment of the present invention is directed to providing a capability for requesting a user to justify an access request, and is referred to herein as an honor agent, as the request for a justification for access relies upon an honor system wherein the user is expected to truthfully explain the justification for the access. Applicants have appreciated that in a computer system sharing context in accordance with the CCOW standard, an advantageous time for requesting a user to justify an access request is in response to a user requesting a change in context, because a user seeking to access new patient information will request a change in context to identify the new patient. In addition, by requesting a user to justify an access request in response to a request to change context, the justification can be provided once for all applications that share the context, rather than requiring the user to interact individually with multiple applications to justify the access request.

Thus, in accordance with one embodiment of the present invention, in response to a user seeking to request a context change, one or more rules or policies can be applied to examine the requested context change to determine whether it may impact privacy concerns as discussed in more detail below (e.g., whether a new user is named, or the user seeks access to information relating to a different patient), and in the event that a condition specified by the rule or policy is determined to exist that may impact privacy concerns, one of several actions can take place. For example, if it is determined by the rule or policy that the requested context change could result in an unauthorized access, the requested change may simply be denied. Alternatively, in order to enable a potential break the glass situation to occur, rather than denying the access outright, the user may be called upon to justify the nature of the authorization for the requested change (e.g., to explain the affiliation with the patient identified in a new context). For example, the user may be requested to enter information that explains the justification for the requested access, or a system may present to the user the information that would be necessary to justify the access and request that the user positively affirm that the required conditions are met if the user provides the requested information or affirmation, the requested context change can be allowed to proceed and the information provided or affirmed by the user can be stored in accordance with an audit facility for later monitoring. If the user refuses to provide or affirm the requested information, the requested context change can either be denied, or the user's refusal can be recorded by an audit facility and highlighted thereby for subsequent investigation.

While one specific embodiment of the present invention described herein relates to the application of a business rule or policy to a requested context change to implement an honor facility as mentioned above and described in more detail below, it should be appreciated that the present invention is not limited in this respect, and that the techniques described herein which apply a business rule to a requested context change, and then either deny the request or request that the user provide or affirm information relating to the requested change, can be used to employ any desired functionality. In this respect, the term business rule or business policy is used herein with respect to non-environmental factors, including any criterion that relates to the behavior of users and the way they interact with the context sharing application programs. The term environmental factors is used herein to refer to technology-based circumstances that may result in a requested context change failing to occur, and may include timeouts and failures of a hardware or software component to function properly. Such circumstances do not relate to defining a business rule or policy that specifies behavior relating to the way in which people interact with the context sharing applications. Thus, the aspects of the present invention described herein can be used in connection with any business rule or policy (which terms are used interchangeably herein) and is not limited to the specific honor requests discussed in detail below.

It should be appreciated that in one embodiment of the present invention, the application of a business rule to a requested context change can lead to a result, and that one or more acts can then be performed in response to that result. As one example, in response to a requested context change in which a user seeks access to information for a new patient, a business rule may be applied that reaches a determination as to whether an affiliation between the user and the patient has previously been established. If the result of the application of the business rule is a determination that an affiliation has previously been established, the action performed in response to that result may be to simply allow the requested context change to proceed. Conversely, if the result of the application of the business rule is a determination that no affiliation has previously been established, the action that may be performed in response to that result may be to deny the request or to request that the user provide or affirm information describing the affiliation. This is merely one example of a type of business rule that can be applied, as well as the type of actions that can be taken in response to a result of the business rule, as the invention is not limited in this respect. Any desired business rule may be applied, and any desired action may be taken in response to a result of the application of the business rule.

It should be appreciated that the aspects of the present invention described herein are not limited to the application of a business rule that results in requesting or gathering information from the user as the final action, as the business rule may take further actions depending upon the information provided or affirmed by the user. For example, referring to the example above wherein a user is requested to provide or affirm an affiliation with a patient in response to a request to change context to access the patient's information, a business rule can be applied that takes different actions depending upon the response of the user. For example, if the user fails to provide or affirm the desired information, an action can be taken that prevents the context change from completing successfully, whereas any of various different actions (e.g., allowing the context change to complete successfully, storing information gathered from the user, adding information gathered from the user into the context, etc.) can be performed when the user provides or affirms the requested information. Thus, aspects of the present invention described herein contemplate the application of one or more business rules in response to the request from a user to change context, including the possibility of gathering information from the user one or more times and taking various actions in response to the results obtained by the application of the business rule(s).

In connection with the embodiment that relates to sharing context in a CCOW environment, it should be appreciated that the CCOW standard provides no facility for one application program (or other software entity) to stop an application requesting a context change from executing the change based on a business rule or policy, as another application could only indirectly cause a requested context change to not complete by failing to communicate properly, which would constitute an environmental factor rather than a business rule or policy. In addition, for the aspect of the present invention that requests that the user provide or affirm additional information in response to a requested context change, the requested information can be information that is in addition to the information defined by the CCOW standard for the sharing of a context.

While one embodiment of the present invention described in detail below relates to context sharing specifically in accordance with the CCOW standard, it should be appreciated that the aspects of the present invention described herein are not limited in this respect, and can be employed in any context sharing system, including those that do not comply with the CCOW standard.

In accordance with one embodiment of the present invention that implements an honor agent for responding to requests to change context, a storage facility may store information relating to the business rule applied so that if a user had previously provided information justifying a particular access request such as the one inherent in a requested context change, the honor facility can rely upon the user's prior representation, and not request information again from the user. For example, if a user had previously specified an affiliation with a particular patient, that representation can be relied upon for future attempts to access the patient information. In accordance with one embodiment of the present invention, a suitable time limit can be imposed so that the information previously provided or affirmed by the user can be relied upon only for that suitable time period, after the expiration of which the user may be requested to provide or affirm the information anew. Of course, it should be appreciated that all aspects of the present invention are not limited to the use of such a time period or even to having the honor facility rely upon prior representations in any respect.

In accordance with one embodiment of the present invention, the manner in which a user may justify access to particular patient data can be specified in any suitable manner (e.g., by specifying a relationship between the user and the patient, between a facility with which the user is associated and the patient, or any other suitable manner) as the present invention is not limited in this respect.

In accordance with one embodiment of the present invention, the nature of the access provided by applications sharing a context can vary depending upon the nature of the authorization that the user specifies. For example, if a user specifies an affiliation with the patient that derives from a consulting relationship, the user may have somewhat limited access to the patient's information, whereas if the user specifies a break the glass emergency access request, all of the patient's records may be made available. It should be appreciated that this is merely an example, and that the manner in which the applications customize the information made available to the user based upon the specified justification for access can be done in any suitable way. In addition, it should be appreciated that the present invention is not limited to use with systems wherein the nature of the information made accessible is customized based upon the specified access justification.

Figure 2:
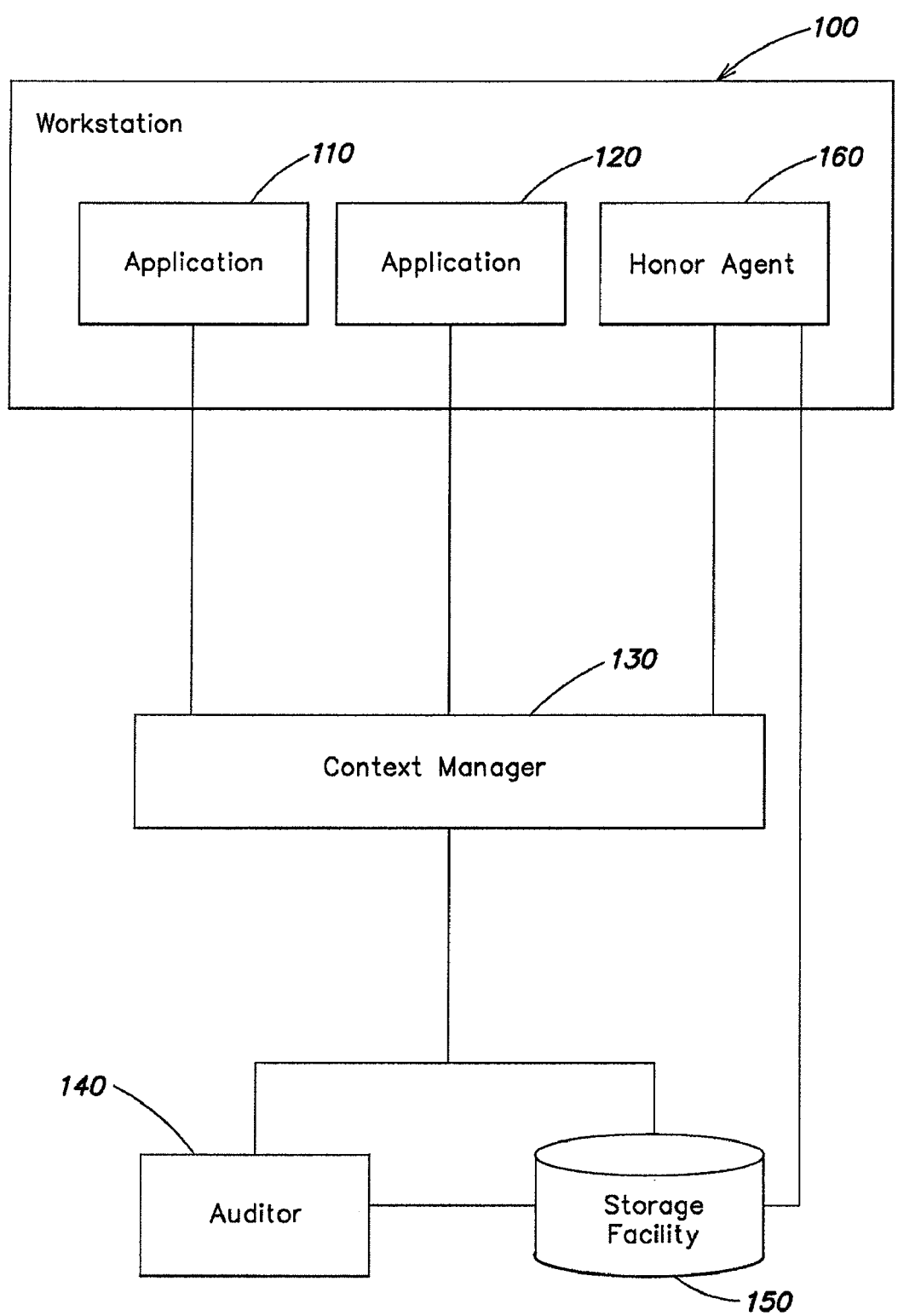
FIG. 2 is a block diagram showing one embodiment of a system having the capability to apply one or more business rules before allowing a context change to complete, according to one embodiment of the invention.

An illustrative implementation of a computer system that includes a context manager to manage context among multiple applications and further includes an honor agent to implement the above-described honor techniques in accordance with one embodiment of the present invention is illustrated in FIG. 2. The system of FIG. 2 is similar in many respects to the system of FIG. 1, and includes a workstation 100 having application programs 110 and 120 executing thereon, as well as a context manager 130 that facilitates the sharing of context between the applications 110 and 120, as well as an auditor 140 and storage facility 150 that perform functions similar to those discussed above in connection with FIG. 1. In one embodiment, the context manager 130 can be provided on a server that is separate from the workstation 100 and can communicate with the workstation 100 over any suitable communication medium, including a private or public network. The auditor 140 can be provided on a same server as the context manager 130 or on any other computing device that can be connected to the context manager over any suitable communication medium, including a private or public network. However, it should be appreciated that the aspects of the present invention described herein are not limited to this or any particular configuration, and that the functional components shown in FIG. 2 can be disposed on the same or different computing devices in any suitable arrangement. In addition, it should be appreciated that each of the functional components described herein can be implemented as the component executing on a single computer, or can be distributed among multiple computers.

In the embodiment illustrated in FIG. 2, the honor agent 160 is shown as installed on the same workstation 100 as the context sharing applications 110, 120. As with the other functional components shown in FIG. 2, the honor agent can be implemented in its entirety on the workstation 100, or can be arranged in other ways. For example, as discussed further below, in accordance with one embodiment of the present invention, the honor agent 160 provides a user interface to a user of the workstation 100 for accessing the applications 110 and 120, so that a module of the honor agent that implements a user interface can be resident on the workstation 100. However, it should be appreciated that other modules of the honor agent can be disposed upon other computing devices and interact with a user interface component in any suitable manner. For example, other modules of the honor agent 160 can execute on a same computer as the context manager 130, or on any other suitable computing device.

It should be appreciated that the application programs 110, 120 can take any form, including application programs that are executed entirely on the workstation or desktop 100, or application programs that have a user interface executing thereon but that interact with components of the application program executing remotely. Examples of different types of applications that may share context are described in U.S. patent application Ser. No. 10/632,673, U.S. Pat. No. 7,577,743, which is incorporated herein by reference. For example, applications 110, 120 may include applications which execute on a web server, with the user interface on the workstation 100 being a browser and/or applications executed on a remote server and emulated on workstation 100 (e.g., using the Citrix MetaFrame and ICA client architecture). These are merely examples, as the aspects of the present invention described herein can be employed with any applications capable of sharing context.

In accordance with one embodiment of the present invention, by including at least a component of the honor agent 160 on the same workstation 100 or desktop as the applications that share a context, the honor agent has the ability to interact with the applications 110, 120 in a manner that prevents the actions of the honor agent from being bypassed when one of the applications 110, 120 seeks to change context. This can be done in any of numerous ways, examples of which are discussed below, and can include the honor agent 160 taking control of the user interface of the workstation 100 so that requirements imposed by the honor agent cannot be bypassed.

In the embodiment shown in FIG. 2, the honor agent 160 communicates with the context manager 130. This communication can be performed over any suitable communication medium, as the present invention is not limited in this respect. In accordance with one embodiment of the present invention, the honor agent 160 may communicate with the context manager 130 over a private or public network. It should be appreciated that public networks often have security techniques (e.g., firewalls) that can make it difficult for components in different security zones (e.g., on opposite sides of a firewall) from directly communicating. In U.S. patent application Ser. No. 10/632,673, U.S. Pat. No. 7,577,743, techniques are described to facilitate communication between the components of a context sharing system in such a network environment. In accordance with one embodiment of the present invention, similar techniques can be employed to facilitate communication between the honor agent 160 and the context manager 130, including through the use of a TCP/IP back channel, which is a durable connection that can be established and maintained between the honor agent 160 and the context manager 130 so that the context manager 130 will have the capability of transmitting communication directly to the honor agent 160 when desired (e.g., when the context manger 130 detects that one of the applications 110, 120 is seeking to change context, so that the honor agent 160 may want to inject itself into that request). It should be appreciated that use of a back channel as described in the above-referenced copending application is merely one technique for facilitating communication between the honor agent 160 and the context manager in a network environment, and that the present invention is not limited to this or any other specific technique, as any suitable technique for facilitating communication can be employed.

In accordance with one embodiment of the present invention, the honor agent 160 has access to a storage facility which stores information related to the business rules that will be applied in response to a requested context change, as well as data that may be used by the honor agent 160 in determining whether to apply those rules in certain circumstances and to guide the application of those rules in the manner described herein. The storage facility can be provided in any suitable location, as the aspects of the present invention described herein are not limited in this respect. In the embodiment shown in FIG. 2, the data and information used by the honor agent 160 is stored in the same storage facility 150 that stores information relating to user accesses to patient information that is audited by the auditor 140. For example, the information and data used by the honor agent 160 may be stored in a database that is co-resident with a database used by the context manager 130 and auditor 140 to store the audit log. However, it should be appreciated that the invention is not limited in this respect, and that the data and information used by the honor agent can be stored elsewhere and in any suitable form.

It should be appreciated that in some embodiments, the data and information used by the honor agent 160 may be stored on a different computer that can be accessed using any suitable communication medium, including a private or public network. As discussed above, public networks can impose security techniques that provide obstacles to direct communication between some components in different security zones (e.g., on opposite sides of a firewall). When the honor agent 160 (or the component thereof that accesses the storage facility 150 when the honor agent is distributed and has a user interface component on the workstation 100 but other components elsewhere) is disposed in a different security zone than the storage facility 150, techniques can be employed to facilitate communication between the honor agent 160 and the storage facility 150, including any of those techniques described above or any other suitable technique, as the present invention is not limited in this respect.

Figure 3:
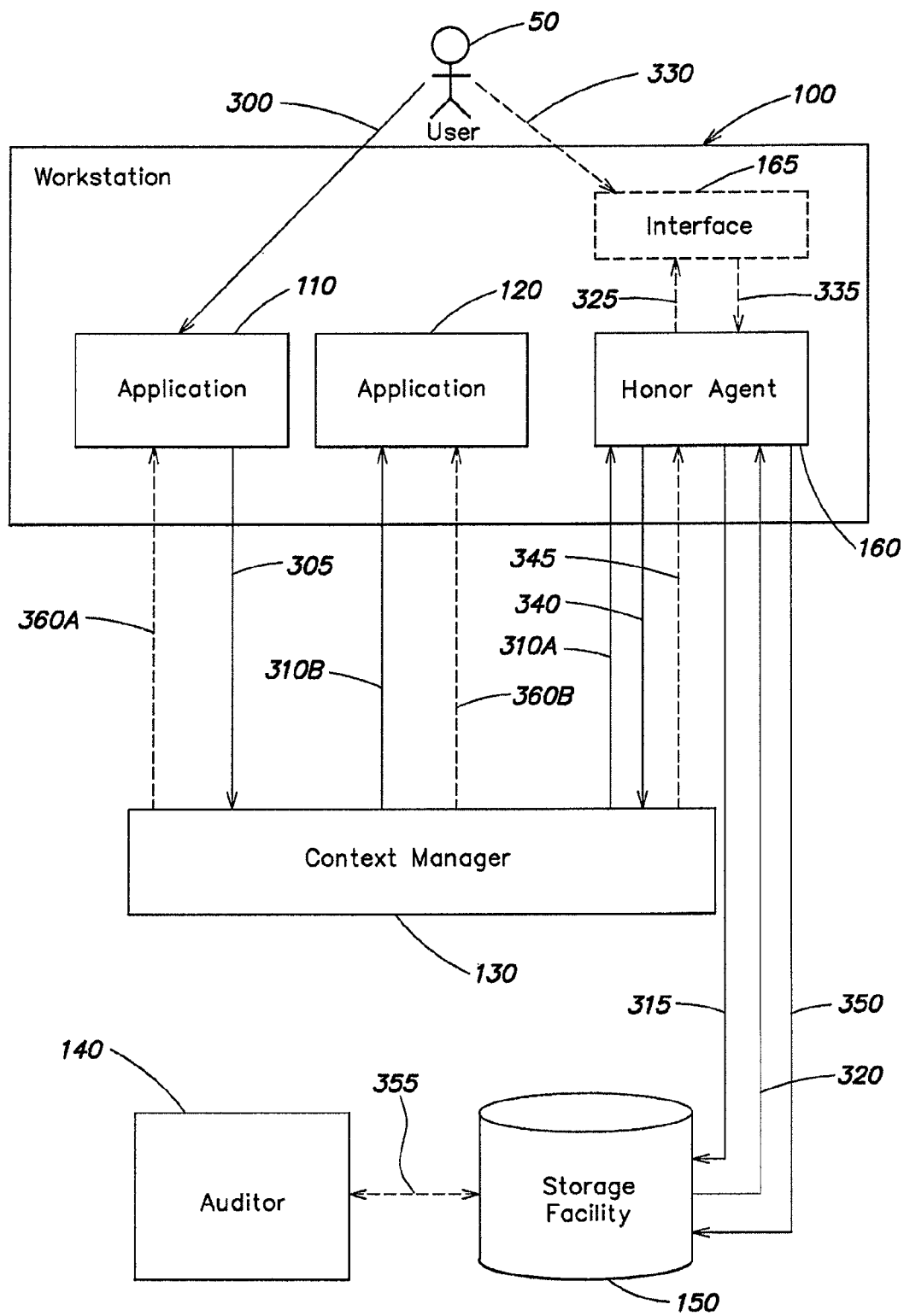
FIG. 3 is a block diagram interaction between components of the system of FIG. 2 in applying one or more business rules before allowing a context change to complete, according to one embodiment of the invention.

Referring first to FIG. 3, as shown by arrow 300, the user 50 employs one of the applications (the application 110 in FIG. 3) to initiate a context change. For example, the user may, via application 110, seek to access to a particular patient's data. In response, as shown by arrow 305, the application 110 may notify the context manager 130 of the request context change. In systems which comply with the CCOW standard, this may be accomplished via the creation of a context change transaction by application 110, and transmission of the context change transaction to context manager 130 for execution.

The honor agent 160 may access information (e.g., stored in storage facility 150) related to the application of business rules to determine the action(s) to take in response to the requested content change. In the description below, the data set accessed by the honor agent will be referred to as the honor agent (HA) data set. The HA dataset may be populated in any suitable way. For example, in accordance with one embodiment of the present invention, the HA data set may be preloaded to provide information relating to an affiliation between users and facilities, between users and patients, and/or between facilities and patients. Alternatively, or in addition, the HA data set may be populated incrementally, as users of the context management system seek to change context, and are requested by the honor agent to provide and/or affirm information relating to their authorization to access patient data in the manner discussed above. For example, the first time a particular user seeks to access a particular patient whose data has not been previously accessed, the honor agent 160 may detect that neither the user or the patient has an affiliation stored in the HA data set and the user may be prompted to provide desired information, such as the facilities with which the patient is affiliated, the facilities with which the user is affiliated, along with justification for the requested access as discussed above. This information may then be stored in the HA data set for future use. While the embodiments of the present invention described herein are not limited in this respect, an example of future use can include the honor agent not going through the process of requesting that a user seeking a context change to access a particular patient's data justify the access request if the HA data set already indicates the nature of the affiliation between the patient and the user.

In accordance with one embodiment of the present invention, information relating to an affiliation (e.g., user to patient, user to facility, facility to patient) may include temporal information related to the affiliation. The temporal information can take any of numerous forms. In accordance with one embodiment of the present invention, temporal information is designed to provide for an expiration of previously-established affiliations. In this respect, in accordance with one embodiment of the present invention, after an affiliation is specified, the honor agent will rely upon a previously specified affiliation and will not request that a user seeking to change context to access data on a patient to which an affiliation has already been established to re-assert the justification for the access request. In accordance with one embodiment of the present invention, the honor agent's reliance on a previously-established affiliation can include a timeout facility, such that a previously-established affiliation (including any of the types of affiliations discussed above) can be limited in time. Temporal information stored in the HA data set to support imposing a timeout restriction on a previously-established affiliation can take any suitable form, as the present invention is not limited in this respect. For example, when an affiliation is established, temporal information may be stored which reflects the current time, and the honor agent can apply any appropriate rule in response to a subsequent access request to determine whether the affiliation may still be relied upon, or whether a timeout situation has occurred wherein the information is stale and the user should be requested to explicitly re-state a justification for the requested access. The time at which an affiliation will expire may be determined at the time an access request is made, at the time affiliation information is provided by a user, or in any other suitable manner. In one embodiment, the timeout or expiration time can be stored in the HA data set. The expiration time can be a function of any suitable business rule, and can be a set time for all affiliations, can vary by user, facility, patient, the nature of the requested access or any other suitable criterion, as the present invention is not limited in this respect.

As discussed above, in accordance with one embodiment of the present invention, when one of the context sharing application programs seeks to change the context, the context manager 130 will be made aware of the change request, and will notify the honor agent 160. In accordance with the embodiment of the present invention that allows for the use of stored affiliations to authorize access rather than requesting access authorization justification from the user for each requested change, the honor agent 160 may access the HA data set to obtain information relating to the affiliation or affiliations relevant to the appropriate business rule that the honor agent will apply to the requested transaction. In accordance with the embodiment that employs a timeout capability for previously-established affiliations, the honor agent 160 will also access the timeout information. If a valid non-expired affiliation has already been established, the honor agent 160 may authorize the context manager 130 to allow the context change transaction to proceed unimpeded. Alternatively, if an appropriate affiliation has not previously been established, or a previously-established affiliation is no longer valid based upon time constraints, the honor agent 160 may act to request information be provided and/or affirmed by the user in any of the ways described herein.

It should be appreciated that the above-described data flow between the context sharing applications 110, 120, the context manager 130 and the honor agent 160 are merely exemplary, as the present invention is not limited to any particular technique, and can be implemented in any suitable manner.

Figure 5:
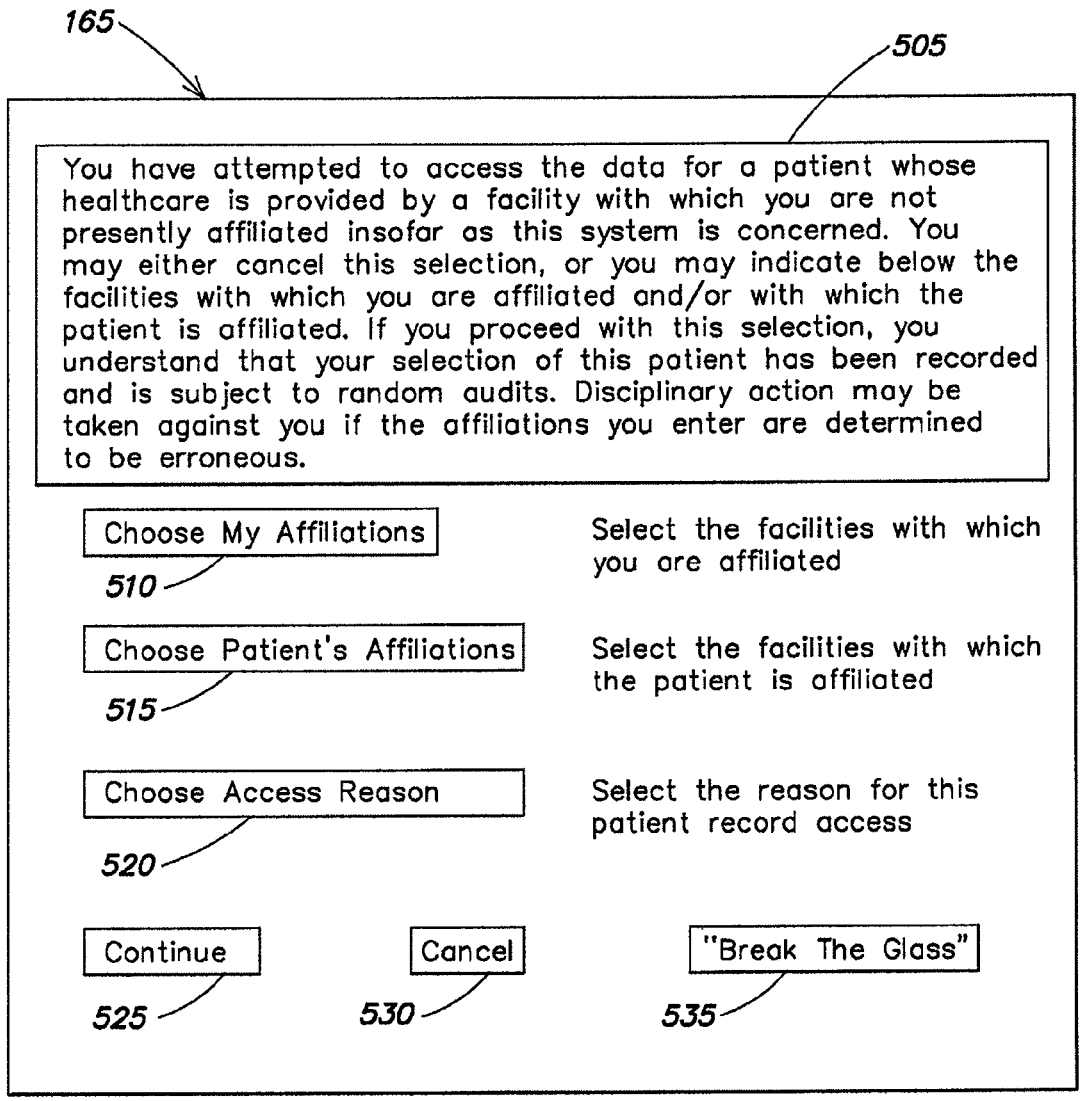
FIG. 5 shows an exemplary interface which may implement one or more business rules before allowing a context change to be completed.

As discussed above, in accordance with one embodiment of the present invention, in response to a request to change context, the honor agent may take action to prevent the requested change from completing successfully unless and until the user has provided and/or affirmed requested information. In accordance with one embodiment of the present invention, a dialogue box such as that shown, for example, in FIG. 5, is presented that forces the user to respond and is incapable of being bypassed, so that the requested context change will not complete successfully unless and until the information requested by the dialogue box has been provided. As discussed above, when the user provides or affirms requested information, the honor agent 160 may update the HA data set with the information for future reference.

There are numerous way in which the honor agent can interact with the context sharing system to prevent a requested context change from completing successfully if a user fails to provide or affirm requested information, and the present invention is not limited to any particular implementation techniques. Two examples are described below, one in which the requested context change is aborted, and another in which actions taken in an attempt to implement the requested context change are allowed to occur, but compensating actions are taken to undo the context change when the user fails to provide or affirm the requested information. In accordance with the latter embodiment, the honor agent takes action to block the user interface (e.g., by presenting the dialogue box as discussed above) so that even if actions relating to the requested context change have been implemented, the user is unable to see any patient data resulting therefrom unless and until the honor agent determines that the user has provided or affirmed the requested information. Of course, the aspect of the present invention that relates to blocking the user interface is not limited in this respect, and can be used in any suitable circumstance, including in connection with the embodiment which aborts a requested context change.

As discussed above, one embodiment of the present invention employs a technique wherein the honor agent does not prevent actions from occurring that actually attempt to implement a requested context change, but takes action (by employing a blocking dialogue box) to prevent the user from seeing the results of any context change until the user has provided or affirmed the requested information, and if the user fails to do so, by taking action that compensates for any of those taken in an attempt to implement the requested context change. In accordance with this embodiment of the present invention, the honor agent can act as another participant in a context, and can communicate in accordance with any protocol previously established for sharing context. An example of such an implementation is described below in connection with FIG. 4 specifically for use in a context sharing system that implements the CCOW standard, but it should be appreciated that the present invention is not limited in this respect, and that similar techniques can be employed in any context sharing system. In accordance with another embodiment of the present invention, the honor agent may hook into the context management system to prevent actions that are performed in the implementation of a context changed to abort the requested change. In accordance with this embodiment of the present invention, some changes to the context management system (e.g., actions taken by the context manager) can be implemented to facilitate the functionality performed by the honor agent. An example of this implementation will now be described in connection with FIG. 3 specifically in a context management system acting in accordance with the CCOW standard. However, it should be appreciated that this aspect of the present invention is not limited to use with a context management system operating in accordance with a the CCOW standard, and can be employed in any context management system.

In response to receipt of the notification of the requested context change, the context manager 130 takes a pair of actions indicated by arrows 310A and 310B, which can be performed simultaneously or in any order. Specifically, as noted at 310A, the context manager notifies the honor agent 160 that a context change has been requested, so that the honor agent can take appropriate action in any of the ways described herein. In addition, the context manager continues with the processing of the request for the context change in the manner established by the context management system. When the context management system complies with the CCOW standard, the communication from the context manager 130 to the application 120 involves a polling operation to determine whether all applications that share a context with application 110 are amenable to the proposed context change. It should be appreciated that the completion of a context change in a context management system in accordance with the CCOW standard can include a number of other types of communication between the applications 110, 120 and the context manager, examples of which are described in U.S. patent application Ser. No. 10/632,673, U.S. Pat. No. 7,577, 743, but will not be described herein or illustrated by communication arrows in FIG. 3 for purposes of clarity. For purposes of this description, it is sufficient to note that such communications may take place, terminating with a notification to the applications 110, 120 that the context has been changed. Such final communication is illustrated conceptually in FIG. 3 with the dotted lines 360A, 360B, which indicate a communication from the context manager 130 to the applications 110, 120. Of course, it should be appreciated that a communication indicating that the context change has been completed may take forms other than communication from the context manager 130 to the applications 110, 120, as the aspects of the present invention described herein are not limited to any particular implementation.

As discussed above, the context manager 130, application programs 110, 120 and honor agent 160 may be implemented on different computers that may communicate via any communication medium, including one or more networks that include security facilities that place these components in different security zones, including an implementation wherein components of the honor agent 160 are installed in a distributed manner such that portions of the honor agent other than the user interface may reside on other devices than the workstation 100. As mentioned above, any suitable technique for facilitating communication between components in different security zones (including the use of back channel communication techniques) may be employed, as the present invention is not limited in this respect.

In response to receipt of the notification at 310A of the requested context change, the honor agent 160 applies a business rule to the requested context change to determine what, if any, actions to take in response thereto. As discussed above, the application of the business rule can include the execution of any suitable instructions, including accessing the HA dataset (e.g., stored in the storage facility 150), information relating to the new or existing context, or any other suitable information, as the aspects of the present invention described herein are not limited in any respect in terms of the nature of the business rule applied, or the information used in applying the rule.

Referring to the example described above wherein the honor agent responds to a request for a context change by applying a business rule that requires the user to provide or affirm information (e.g., an affiliation of the user with a new patient) before allowing the context change to complete successfully, the business rule executed by the honor agent 160 may be defined by instructions stored in any suitable location (e.g., in the HA dataset or elsewhere) and can include examining information stored in the HA dataset (e.g., when the user has a previously-established affiliation with the new patient that has not expired) as well as information contained in the new context (e.g., the patient identified for the context switch). The accessing of information from the HA dataset, which may be in the storage facility 150 in FIG. 3 as discussed above, is illustrated conceptually by the communication arrow 320 in FIG. 3.

As discussed above, as a result of application of the business rule, the honor agent 160 may determine that the requested context change should proceed unimpeded (e.g., if the information in the HA dataset indicates that the user has a valid unexpired affiliation with the new patient) or may require that the user provide an affirmative representation relating to a justification for the requested context change before proceeding. As further discussed above, when the latter situation arises, the honor agent may present a user interface to the user to gather the desired information. This is shown conceptually in FIG. 3, via the interface 165 that is made available to the user via an action 325 of the honor agent. The interface 165 can take any suitable form, as the aspects of the present invention described herein are not limited in this respect. An exemplary interface 165 is shown in FIG. 5 and will be described in further detail below. This interface of FIG. 5 is provided for illustrative purposes only, as an interface may take any of numerous forms.

As discussed above, if the user fails to provide or affirm the information presented by the user interface, the honor agent may refuse to allow the requested context change to complete successfully. As discussed above, in connection with the embodiment of FIG. 3, the application programs 110, 120 and the context manager 130 can, in parallel with the honor agent applying the desired business rules, take the actions normally specified by the context management system to respond to the requested context change, and may complete those actions in a manner that would normally result in successful completion of the context change. However, as discussed above, the interface 165 can be presented as a dialogue box on the workstation 100 so that user 150 will not have access to any information resulting from the requested context change.

In addition, honor agent 160 can take any desired action to compensate for the actions taken in attempting to complete the requested context change, so that the requested change ultimately does not complete successfully. The nature of the compensating actions may vary depending upon the nature of the context management system and can take any form, as the aspects of the present invention described here are not limited in this respect. In accordance with one aspect of the embodiment of the present invention, the honor agent 160 can inform the context manager 130 (in a communication labeled 340 in FIG. 3) that compensating actions for the requested context change should be executed, and the context manager, via communications with the application programs 110 and 120 can perform such compensating actions.

The user may respond (as shown conceptually by the dotted line 330 in FIG. 3) to the information requested by the honor agent interface 165 in any suitable manner. For example, the user may input information by a keyboard, voice recognition system, mouse clicks, touch screen, or any other technique, as the present invention is not limited in this respect. When the user provides the desired information via the interface 165, the information is passed (as shown conceptually at 335 in FIG. 3) to the honor agent 160 so that the honor agent may take suitable action. For example, the honor agent may simply remove the interface 165 so that the user has access to the applications 110, 120 that have completed the context change, the honor agent may inform the context manager 130 that the context change can proceed to successful completion and/or the honor agent may store in the HA dataset information recording the information provided or affirmed by the user 50. Any such information recorded in the HA dataset may, in accordance with one embodiment of the present invention, be made available to an audit capability, such as the auditor 140, as shown conceptually with arrow 355 in FIG. 3.

As discussed above, the information stored in the HA dataset and made available to an auditing facility may take any form, as the present invention is not limited in this respect. As discussed above, the audit facility may be capable of auditing information based on any of numerous criteria, including information recording the justification that a user provided for accessing particular patient data. For example, the auditor may prepare reports and be particularly sensitive to users that specified a break the glass emergency situation to justify access to a particular patient record, or based on any other suitable criteria, as the present invention is not limited in this respect.

In accordance with one embodiment of the present invention, the honor agent may take the further action of inserting data into a context information that relates to the information provided or affirmed by the user in justifying the requested context change. For example, the honor agent can add data to the context information relating to any of the types of affiliations discussed above, including an affiliation between the user and patient, the user and a health care facility, and/or a health care facility and the patient. Such data can be added in any suitable way, as the present invention is not limited in this respect. In one illustrative example for use in a context management system that operates in accordance with the CCOW standard, a new subject can be created that is of an identifier type, as it identifies a patient record access event. The subject may be dependent upon the patient subject, or may be implemented as an independent subject. The types of information that may be provided in the new subject can include, as discussed above, a user affiliation, a patient affiliation, and/or the justification that a user gave for seeking access to the patient data at a particular point in time.

In accordance with one embodiment of the present invention, one or more of the applications 110, 120 may be configured to recognize the information provided or affirmed by the user to justify a context change (e.g., when the data is added to the context it may become visible to the application programs 110, 120) and to change the behavior and/or functionality based thereupon. For example, in accordance with one embodiment of the present invention, when an emergency or break the glass access request is specified by the user, one or more of the application programs 110, 120 may be configured to facilitate access to all patient information to facilitate an emergency response. It should be appreciated that this is simply one example of the ways in which the context of sharing applications can respond to information provided or affirmed by the user in requesting a context change, as numerous other examples are possible, as the aspect of the present invention directed to this modified behavior and/or functionality of the context sharing application is not limited in this respect.

As discussed above, one aspect of the technique for preventing successful completion of a requested context change without the user providing or affirming the information is that it can be employed as a supplement to an existing context management system, without requiring hooking into or modifying the context management system. Some context management systems may have communication timeouts built into their architecture, including both message-level timeouts (e.g., those that relate to communications from one component of the system to another) and transaction level timeouts that bracket various phases of a context changed transaction. In accordance with one embodiment of the present invention, techniques are employed for dealing with potential communication timeouts provided by a context management system while seeking to ensure that no access request goes unaudited and that a user-friendly environment is maintained. While advantageous, it should be appreciated that the present invention is not limited in this respect, and that a context management system include alternatively being modified so that timeout issues may not be dealt with and/or the technique described herein can be employed with a context management system that does not employ communication timeouts.

In a first embodiment for dealing with a timeout situation, the honor agent 160 may present the interface 165 (e.g., the dialog as discussed above) for a period of time less than the timeout period established by the context management system for performing the context management system activities relating to processing the request for a change in context. For example, if the context management timeout period is ten seconds, the honor agent 160 may present the interface 165 for seven seconds, to ensure that the user need respond to the honor agent before the expiration of the context management timeout. If the user does not respond to the honor agent interface 165 during the specified timeout period, the honor agent interface 165 may be removed and the requested context change can be prevented from completing successfully (e.g., by compensating for any actions taken or aborting the requested context change). Thus, in order to execute a context change to see a new patient data, the user will need to select the patient again.

In an alternative approach, the honor agent may employ the interface 165 to block the user from seeing any new patient data that results from a requested context change in the manner discussed above, and provides its own timeout feature for the interface 165 that can be any length of time, including a length of time longer than the timeouts established by the context management system. This approach can be employed when a response from the honor agent 160 verifying that a requested context change is authorized is employed by the context management system, such that the context management system may proceed as if the honor agent were not present and complete a requested context change in its typical manner, such that timeout issues within the context management system are of no concern. Since the interface 165 will prevent the user from seeing any new patient data resulting from a requested context change, unaudited access to the new data is prevented, and any desired timeout period (including no timeout at all) can be applied to the maintenance of the interface 165 by the honor agent.

As discussed above, in accordance with one embodiment of the present invention, a requested context change can be prevented from completing successfully if the user does not provide or affirm information requested by the honor agent by either aborting the requested context change or taking compensating actions. In accordance with one embodiment of the present invention, compensating actions can include the honor agent initiating a context change operation to change the context back to the context that existed before the user requested the change that was ultimately prevented from completing successfully. It should be appreciated from the foregoing that it is possible that the compensating context change can timeout. To address such a concern, in accordance with one embodiment of the present invention, when the context manager sees a request from the honor agent to change context, it can immediately switch the patient context to an empty context, so that if the compensating request for a context change timesout, the user is not given access to any patient data, thereby preventing the user from accessing the patient data the user sought to access but was prevented from accessing by the honor agent.

As discussed above, in an alternate embodiment of the invention, rather than preventing a requested context change from completing successfully by performing compensating actions, one embodiment of the present invention is directed to a technique that aborts a requested context change if a user fails to provide or affirm the information requested by the honor agent. This aspect of the present invention can be implemented in any suitable manner, as the invention is not limited to any particular implementation technique. In accordance with one embodiment of the present invention, techniques can be employed that hook into the context management system and prevent the completion of actions employed thereby to implement a context change. These communications can include communications between the context sharing applications 110, 120 and the context manager 130, or any communications that, when blocked, will prevent the completion of a context change, as the present invention is not limited in this respect.

Figure 4:
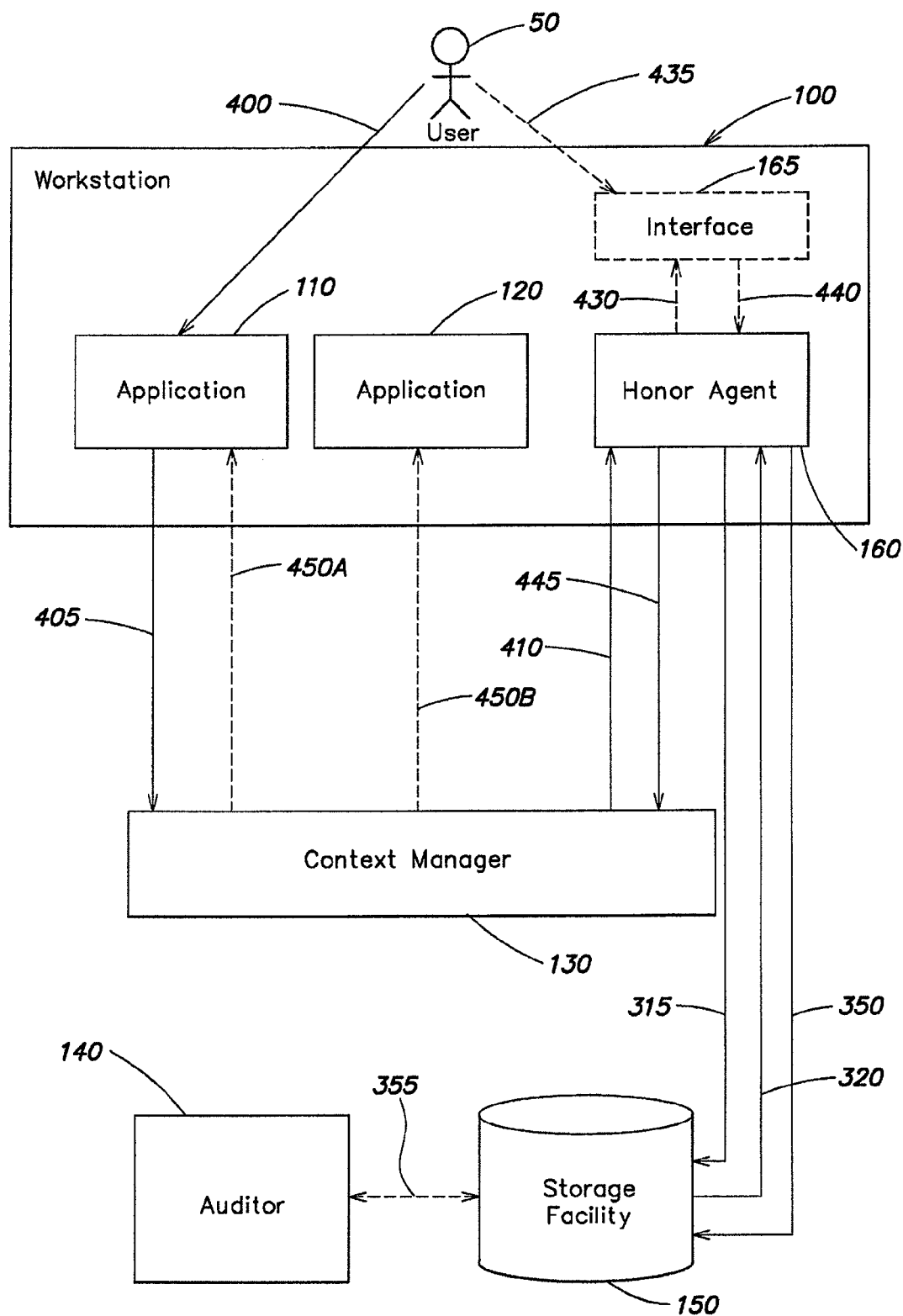
FIG. 4 is a block diagram showing interaction between components of the system of FIG. 2 in applying one or more business rules before allowing the completion of a context change, according to another embodiment of the invention.

One illustrative implementation of the embodiment of present invention that aborts requested context change will now be described referring to FIG. 4, wherein context sharing may be implemented in accordance with CCOW standards. Initially, a user 50 of application program 110 requests a change in context, for example to access data for a new patient. As shown at 405, the application program 110 may notify the context manager 130 of the requested context change. Rather than simply taking the normal action of querying the other applications sharing context as to whether the requested change is acceptable, the context manager (as shown at 410) can inform the honor agent 160 of the requested context change, and wait a response from the honor agent 160 before proceeding. The honor agent may (as illustrated at 430) provide an interface 165 to the user, requesting the user (at 435) provide or affirm information justifying the context change, which can then be relayed to the honor agent 160 (illustrated at 440). The honor agent 160 may present the user interface 165 in much the same manner as discussed above. However, because the embodiment described in connection with FIG. 4 prevents a requested context change from completing, there is no concern that the user will gain unaudited access to the new patient data on the display screen, so that the interface 165 need not block the display of information presented by the context sharing applications, although such an implementation in this embodiment is of course possible.

The manner in which the honor agent applies a business rule to the requested context change, based potentially on information stored in the HA dataset (e.g., stored in the storage facility 150), information in either the old or new context, or any other information can be performed in much the same manner as discussed above. For example, communication between honor agent 160 and storage facility 150 may occur as indicated at 315 and 320, as described above with reference to FIG. 3.

When the user provides or affirms information via the interface 165 required by the honor agent 160, the honor agent may inform the context manager (as shown at 445) that the requested context change can proceed, at which point the context manager 130 may implement the context change in the usual way. As discussed above, in accordance with one embodiment of the present invention, information provided or affirmed by the user may be added to the context (as well as potentially being stored in the HA dataset), such that this information can be provided by the honor agent 160 to the context manager or any other suitable component in much the same manner as discussed above.

When the user fails to provide or affirm the information required by the honor agent 160, the honor agent may inform the context manager 130 (illustrated at 445) that the requested context change is denied, such that the context manager 130 can then abort the requested context change in any suitable manner (e.g., by informing the user 50 via the requesting application 110 that the requested context change has been denied).

Again, the above-described example is provided merely for illustrative purposes, as the aspect of the present invention that aborts requested context changes in the absence of a user providing or affirming information can be implemented in any of numerous ways, and is not limited to this specific example discussed above or to use with a context management system operating in accordance with the seek how standard.

As discussed above, the interface 165 presented by the honor agent can take any of numerous forms, as the present invention is not limited to any particular interface, either in terms of the technical manner in which information is exchanged with the user, the content of the information that the user is asked to provide and/or affirm, or the configuration of the interface. An exemplary interface 165 is illustrated in FIG. 5. The interface 165 includes warning text 505 that may be customized for each installation, and that provides a warning to the user that they are expected to provide the information truthfully, and that their response may be audited.

In the embodiments shown, interface 165 also includes portions 510 and 515, which request the user to specify affiliations for the user and patient, respectively. In one embodiment, the portions 510 and 515 may be drop-down boxes that are populated with options from which the user may select. However, these portions can be implemented in any suitable way, including through the use of fields requiring that the user enter information describing the specified affiliations.

The illustrative interface shown in FIG. 5 further includes a portion 520 that requested that the user specify a reason for the patient record access. As with the portions 510 and 515, the portion 520 can be implemented as a drop-down box which represents options from which the user can select, or may take any other form, including a field in which a user can provide information specifying the reason for the access.

The interface 165 illustrated in FIG. 5 further includes a continue box 525 that a user can select (e.g., with a mouse click) after providing information for the other fields to submit the information for processing by the honor agent, as well as a cancel field 530 that a user can select to cancel the requested context change. For example, a user that sought unauthorized access to patient information accidentally may be alerted to such a fact to the presentation of the interface 165 and may choose to cancel their request.

Finally, the illustrative interface shown in FIG. 5 includes the "break the glass" field 535 that can enable emergency access in the manner discussed above. It should be appreciated that "break the glass" access can alternatively be provided as one of the access reasons to choose. In field 520, but that the separate field 535 can optionally be provided to facilitate quick user access in the event of an emergency.

It should be appreciated that in some cases, no affiliations may previously have been stored for either a user or a patient. In such a circumstance, the user interface 165 can provide the capability for a user to enter affiliations for the user and/or patient.

As discussed above, the aspects of the present invention described herein that relate to implementing an honor system that requests a user to justify an attempted access request and response to a context change are not limited to use with a CCOW system, and can be employed in connection with any context management system.

In addition, the aspects of the present invention described herein are not limited to use with implementing an honor facility, as an agent or other component in a context management system may respond to a request for a context change by applying any suitable business rule, and by taking any suitable action, such that the aspects of the present invention are not limited to taking an action that denies a requested context change. For example, aspects of the present invention can apply business rules that request that information be provided or affirmed relating to a requested context change, and/or can involve the generation of one or more alerts or the adding into the context of additional information. Numerous other uses are possible. For example, in response to a request from a user to change context to access records for a patient, the business rule may apply that accesses records of the patient and presents the user with information relevant thereto, such as whether the patient is insured, if so, the identity of the insurance company, notifying the user of potential passed payment problems, etc., and may then ask the user whether they wish to continue.

As another example, in response to a request for a context change to access a particular system, the agent may query the user on whether the user has been trained on a new system, and may or may not choose to deny access if the user does not specify that they have been trained on the new system.

As a further example, in a response to a request to change context to a new patient, relevant information about the patient may be highlighted to the user, such as notifying the user of particular allergies or other significant health aspects of the patient.

Again, the above examples are merely illustrative, as the present invention is not limited in this respect. In this respect, the aspects of the present invention can relate to an agent that, in response to a request of context change, can provide an interface to the user based upon any suitable business rule, with the business rule being based upon any suitable factors, such as, stored information relating to the user, the patient, or any other aspect of the context, based upon information in either the new or used context, or any other suitable factor. The interface presented by the agent may regulate access to the information in the context, including a complete denial of access in situations that do not impact health issues necessitating a "break the glass" emergency type of scenario. In addition, the interface can request any desired information from the user, or can alert the user to information of which the user should be cognizant, and optionally require the user to acknowledge or affirm.

As should be appreciated from the foregoing, one embodiment of the invention is directed to use in a computer system comprising two or more software applications that share context. The applications can share context in any suitable manner, as the aspects of the present invention described herein are not limited in this respect. For example, the applications can include native context-sharing functionality to facilitate sharing context in accordance with the CCOW standard (or any other context-sharing protocol), or one or more of the software applications cannot provide context-sharing functionality natively, but can work in the computer system with a bridge or other component that interfaces with the application program and provides context-sharing functionality that enables the application program to share context with one or more other applications.

The above-described embodiments of the present invention can be implemented in any of numerous ways. For example, the embodiments may be implemented using hardware, software or a combination thereof. For example, one or more processors provided in a single computer or distributed among multiple computers may be programmed using software code to perform one or more aspects of the invention. It should be appreciated that any component or collection of components that perform the functions described above can be generically considered as one or more controllers that control the above-discussed function. The one or more controllers can be implemented in numerous ways, such as with dedicated hardware, or with general purpose hardware (e.g., one or more processors) that is programmed using microcode or software to perform the functions recited above.

It should be appreciated that the various methods outlined herein may be coded as software which is executable on one or more processors that employ any one of a variety of operating systems or platforms. Additionally, such software may be written using any of a number of suitable programming languages and/or conventional programming or scripting tools, and also may be compiled as executable machine language code. In this respect, it should be appreciated that one embodiment of the invention is directed to a computer-readable medium (or multiple computer-readable media), such as computer memory, floppy disk(s), compact disk(s), optical disk(s), magnetic tape(s), and/or other media, which are encoded with one or more programs that, when executed on one or more computers or other processors, perform methods that implement the various embodiments of the invention discussed above. The computer-readable medium or media can be transportable, such the program or programs stored thereon can be loaded onto one or more different computers or other processors to implement various aspects of the present invention as discussed above.

It should be understood that the terms "application" and "program" and "software" are used herein in a generic sense to refer to any type of computer code or set of instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Various aspects of the present invention may be implemented alone, in combination, or in a variety of arrangements not specifically described in the foregoing. The present invention is therefore not limited in its application to the details and arrangement of components set forth in the foregoing description or illustrated in the drawings. The invention is capable of other embodiments and of being practiced or of being carried out in various ways. Accordingly, the foregoing description and drawings are by way of example only, and it is to be appreciated that various alterations, modifications, and improvements will readily occur to those skilled in the art. Such alterations, modifications, and improvements are intended to be part of this disclosure, and are intended to be within the spirit and scope of the invention.

Also, the phraseology and terminology used herein is for the purpose of description and should not be regarded as limiting. The use of "including," "comprising," or "having," "containing," "involving," and variations thereof herein, is meant to encompass the items listed thereafter and equivalent thereof as well as additional items.

The invention claimed is:

1. In a computer system comprising at least two software applications sharing context, wherein a context change may be requested by a user of at least one of the at least two software applications, a method comprising acts of:
   (A) in response to the user requesting a change from a first context to a second context, applying at least one business rule to at least a portion of the first context and/or to at least a portion of the second context to obtain at least one result from the application of the business rule; and
   (B) in response to the at least one result, performing at least one act selected from the group consisting of:
   denying the request to change from the first context to the second context;
   requesting the user to provide information relating to the requested change; and
   requesting the user to affirm information relating to the requested change.

2. The method of claim 1, wherein the act (B) comprises, in response to the at least one result, performing the act of denying the request to change from the first context to the second context.

3. The method of claim 1, wherein the act (B) comprises, in response to the at least one result, performing the act of requesting the user to provide information relating to the requested change.

4. The method of claim 3, further comprising an act of:
   (C) in response to the user providing the requested information relating to the requested change, storing the information.

5. The method of claim 3, wherein the second context relates to at least one patient, and wherein the act (B) comprises, in response to the at least one result, requesting the user to provide information specifying a clinical relationship between the user and the at least one patient.

6. The method of claim 4, wherein the computer system further comprises an auditor capable of extracting information relating to user access to patient records, and wherein the act (C) comprises an act of storing the information in a data set accessible to the auditor.

7. The method of claim 4, further comprising an act of:
   (D) auditing the information.

8. The method of claim 1, wherein the act (B) comprises, in response to the at least one result, performing the act of requesting the user to affirm information relating to the requested change.

9. The method of claim 8, further comprising an act of:
(C) in response to the user affirming the information relating to the requested change, storing the information.

10. The method of claim 8, wherein the second context relates to at least one patient, and wherein the act (B) comprises, in response to the at least one result, requesting the user to affirm information specifying a clinical relationship between the user and the at least one patient.

11. The method of claim 9, wherein the computer system further comprises an auditor capable of extracting information relating to user access to patient records, and wherein the act (C) comprises an act of storing the information in a data set accessible to the auditor.

12. The method of claim 9, further comprising an act of:
(D) auditing the information.

13. The method of claim 1, wherein the act (A) comprises an act of applying the at least one business rule to at least a portion of the first context to obtain the at least one result.

14. The method of claim 1, wherein the act (A) comprises an act of applying the at least one business rule to at least a portion of the second context to obtain the at least one result.

15. The method of claim 1, wherein the act (A) comprises an act of applying the at least one business rule to at least a portion of the first context and to at least a portion of the second context to obtain the at least one result.

16. The method of claim 1, wherein the computer system further comprises a context manager that manages context sharing between the at least two software applications.

17. The method of claim 1, wherein the act (B) comprises, in response to the at least one result, performing at least one act selected from the group consisting of:
requesting the user to provide information relating to the requested change; and
requesting the user to affirm information relating to the requested change; and
wherein the method further comprises an act of:
(C) when the user fails to either provide or affirm the requested information, performing an act of preventing the requested context change from completing successfully.

18. The method of claim 17, wherein the act (C) comprises an act of aborting the requested context change.

19. The method of claim 17, wherein the act (C) comprises an act of compensating for any actions taken in an attempt to implement the requested context change.

20. The method of claim 17, wherein the user interacts with the at least two software applications via a user interface, and wherein the act (B) comprises locking the user interface so that the user cannot gain access to at least some information presented by at least one of the at least two software applications until the user either provides or affirms the requested information.

21. The method of claim 1, wherein the act (B) comprises, in response to the at least one result, performing at least one act selected from the group consisting of:
requesting the user to provide information relating to the requested change; and
requesting the user to affirm information relating to the requested change; and
wherein the method further comprises an act of:
(C) when the user provides or affirms the requested information, performing an act of adding into the second context at least some data based, at least in part, on the information provided or affirmed by the user.

22. The method of claim 21, wherein the act (C) comprises an act of adding into the second context the at least some data based, at least in part, on the information provided or affirmed by the user and the at least one business rule.

23. The method of claim 21, wherein the act (C) comprises an act of adding the at least some data into a subject in the second context that relates to user attempts to access patient records.

24. The method of claim 1, wherein the second context relates to at least one patient, and wherein the act (B) comprises, in response to the at least one result, performing the act of requesting the user to provide information specifying a clinical relationship between the user and the at least one patient.

25. The method of claim 1, wherein one or more of the at least two software applications includes no native context-sharing functionality, and wherein the computer system comprises a component that enables the one or more software applications to share context with other of the at least two software applications.

26. The method of claim 1, wherein the at least two software applications share context in accordance with a context-sharing protocol other than a CCOW standard.

27. At least one computer-readable medium encoded with instructions which, when executed in a computer system comprising at least two software applications sharing context, wherein a context change may be requested by a user of at least one of the at least two software applications, perform a method comprising acts of:
(A) in response to the user requesting a change from a first context to a second context, applying at least one business rule to at least a portion of the first context and/or to at least a portion of the second context to obtain at least one result from the application of the business rule; and
(B) in response to the at least one result, performing at least one act selected from the group consisting of:
denying the request to change from the first context to the second context;
requesting the user to provide information relating to the requested change; and
requesting the user to affirm information relating to the requested change.

28. The at least one computer-readable medium of claim 27, wherein the act (B) comprises, in response to the at least one result, performing the act of denying the request to change from the first context to the second context.

29. The at least one computer-readable medium of claim 27, wherein the act (B) comprises, in response to the at least one result, performing the act of requesting the user to provide information relating to the requested change.

30. The at least one computer-readable medium of claim 29, further comprising an act of:
(C) in response to the user providing the requested information relating to the requested change, storing the information.

31. The at least one computer-readable medium of claim 30, wherein the computer system further comprises an auditor capable of extracting information relating to user access to patient records, and wherein the act (C) comprises an act of storing the information in a data set accessible to the auditor.

32. The at least one computer-readable medium of claim 30, further comprising an act of:
(D) auditing the information.

33. The at least one computer-readable medium of claim 29, wherein the second context relates to at least one patient, and wherein the act (B) comprises, in response to the at least one result, requesting the user to provide information specifying a clinical relationship between the user and the at least one patient.

34. The at least one computer-readable medium of claim 27, wherein the act (B) comprises, in response to the at least one result, performing the act of requesting the user to affirm information relating to the requested change.

35. The at least one computer-readable medium of claim 34, further comprising an act of:
  (C) in response to the user affirming the information relating to the requested change, storing the information.

36. The at least one computer-readable medium of claim 34, wherein the second context relates to at least one patient, and wherein the act (B) comprises, in response to the at least one result, requesting the user to affirm information specifying a clinical relationship between the user and the at least one patient.

37. The at least one computer-readable medium of claim 35, wherein the computer system further comprises an auditor capable of extracting information relating to user access to patient records, and wherein the act (C) comprises an act of storing the information in a data set accessible to the auditor.

38. The at least one computer-readable medium of claim 35, further comprising an act of:
  (D) auditing the information.

39. The at least one computer-readable medium of claim 27, wherein the act (A) comprises an act of applying the at least one business rule to at least a portion of the first context to obtain the at least one result.

40. The at least one computer-readable medium of claim 27, wherein the act (A) comprises an act of applying the at least one business rule to at least a portion of the second context to obtain the at least one result.

41. The at least one computer-readable medium of claim 27, wherein the act (A) comprises an act of applying the at least one business rule to at least a portion of the first context and to at least a portion of the second context to obtain the at least one result.

42. The at least one computer-readable medium of claim 27, wherein the computer system further comprises a context manager that manages context sharing between the at least two software applications.

43. The at least one computer-readable medium of claim 27, wherein the act (B) comprises, in response to the at least one result, performing at least one act selected from the group consisting of:
  requesting the user to provide information relating to the requested change; and
  requesting the user to affirm information relating to the requested change; and
  wherein the method further comprises an act of:
    (C) when the user fails to either provide or affirm the requested information, performing an act of preventing the requested context change from completing successfully.

44. The at least one computer-readable medium of claim 43, wherein the act (C) comprises an act of aborting the requested context change.

45. The at least one computer-readable medium of claim 43, wherein the act (C) comprises an act of compensating for any actions taken in an attempt to implement the requested context change.

46. The at least one computer readable medium of claim 43, wherein the user interacts with the at least two software applications via a user interface, and wherein the act (B) comprises locking the user interface so that the user cannot gain access to at least some information presented by at least one of the at least two software applications until the user either provides or affirms the requested information.

47. The at least one computer-readable medium of claim 27, wherein the act (B) comprises, in response to the at least one result, performing at least one act selected from the group consisting of:
  requesting the user to provide information relating to the requested change; and
  requesting the user to affirm information relating to the requested change; and
  wherein the method further comprises an act of:
    (C) when the user provides or affirms the requested information, performing an act of adding into the second context at least some data based, at least in part, on the information provided or affirmed by the user.

48. The at least one computer-readable medium of claim 47, wherein the act (C) comprises an act of adding into the second context the at least some data based, at least in part, on the information provided or affirmed by the user and the at least one business rule.

49. The at least one computer-readable medium of claim 47, wherein the act (C) comprises an act of adding the at least some data into a subject in the second context that relates to user attempts to access patient records.

50. The at least one computer-readable medium of claim 27, wherein the second context relates to at least one patient, and wherein the act (B) comprises, in response to the at least one result, performing the act of requesting the user to provide information specifying a clinical relationship between the user and the at least one patient.

51. The at least one computer-readable medium of claim 27, wherein one or more of the at least two software applications includes no native context-sharing functionality, and wherein the computer system comprises a component that enables the one or more software applications to share context with other of the at least two software applications.

52. The at least one computer-readable medium of claim 27, wherein the at least two software applications share context in accordance with a context-sharing protocol other than a CCOW standard.

53. An agent for use in a computer system comprising at least two software applications sharing context, wherein a context change may be requested by a user of at least one of the at least two software applications, the agent comprising:
  at least one processor programmed to, in response to the user requesting a change from a first context to a second context;
    apply at least one business rule to at least a portion of the first context and/or to at least a portion of the second context to obtain at least one result from the application of the business rule; and
    in response to the at least one result, perform at least one act selected from the group consisting of:
      denying the request to change from the first context to the second context;
      requesting the user to provide information relating to the requested change; and
      requesting the user to affirm information relating to the requested change.

54. The agent of claim 53, wherein the at least one processor is programmed to, in response to the at least one result, perform the act of denying the request to change from the first context to the second context.

55. The agent of claim 53, wherein the at least one processor is programmed to, in response to the at least one result, perform the act of requesting the user to provide information relating to the requested change.

56. The agent of claim 55, wherein the at least one processor is programmed to, in response to the user providing the requested information relating to the requested change, store the information.

57. The agent of claim 55, wherein the second context relates to at least one patient, and wherein the at least one processor is programmed to, in response to the at least one result, request the user to provide information specifying a clinical relationship between the user and the at least one patient.

58. The agent of claim 56, wherein the computer system further comprises an auditor capable of extracting information relating to user access to patient records, and wherein the at least one processor is programmed to store the information in a data set accessible to the auditor.

59. The agent of claim 56, in combination with the computer system, wherein the computer system further comprises:
an auditor that audits the information.

60. The agent of claim 53, wherein the at least one processor is programmed to, in response to the at least one result, perform the act of requesting the user to affirm information relating to the requested change.

61. The agent of claim 60, wherein the at least one processor is programmed to, in response to the user affirming the information relating to the requested change, store the information.

62. The agent of claim 60, wherein the second context relates to at least one patient, and wherein the at least one processor is programmed to, in response to the at least one result, request the user to affirm information specifying a clinical relationship between the user and the at least one patient.

63. The agent of claim 61, wherein the computer system further comprises an auditor capable of extracting information relating to user access to patient records, and wherein the at least one processor is programmed to store the information in a data set accessible to the auditor.

64. The agent of claim 61, in combination with the computer system, wherein the computer system further comprises:
an auditor that audits the information.

65. The agent of claim 53, wherein the at least one processor is programmed to apply the at least one business rule to at least a portion of the first context to obtain the at least one result.

66. The agent of claim 53, wherein the at least one processor is programmed to apply the at least one business rule to at least a portion of the second context to obtain the at least one result.

67. The agent of claim 53, wherein the at least one processor is programmed to apply the at least one business rule to at least a portion of the first context and to at least a portion of the second context to obtain the at least one result.

68. The agent of claim 53, in combination with the computer system, wherein the computer system further comprises a context manager that manages context sharing between the at least two software applications.

69. The agent of claim 53, wherein the at least one processor is programmed to, in response to the at least one result, perform at least one act selected from the group consisting of requesting the user to provide information relating to the requested change and requesting the user to affirm information relating to the requested change; and
wherein the at least one processor is further programmed to, when the user fails to either provide or affirm the requested information, prevent the requested context change from completing successfully.

70. The agent of claim 69, wherein the at least one processor is programmed to prevent the requested context change from completing successfully by aborting the requested context change.

71. The agent of claim 69, wherein the at least one processor is programmed to prevent the requested context change from completing successfully by compensating for any actions taken in an attempt to implement the requested context change.

72. The agent of claim 69, wherein the user interacts with the at least two software applications via a user interface, and wherein the at least one processor is programmed to block the user interface so that the user is incapable of accessing at least some information presented by at least one of the at least two software applications until the user either provides or affirms the requested information.

73. The agent of claim 53, wherein the at least one processor is programmed to, in response to the at least one result, perform at least one act selected from the group consisting of requesting the user to provide information relating to the requested change and requesting the user to affirm information relating to the requested change; and
wherein the at least one processor is further programmed to, when the user provides or affirms the requested information, add into the second context at least some data based, at least in part, on the information provided or affirmed by the user.

74. The agent of claim 73, wherein the at least one processor is programmed to, when the user provides or affirms the requested information, add into the second context the at least some data based, at least in part, on the information provided or affirmed by the user and the at least one business rule.

75. The agent of claim 73, wherein the at least one processor is programmed to add the at least some data into a subject in the second context that relates to user attempts to access patient records.

76. The agent of claim 53, wherein the second context relates to at least one patient, and wherein the at least one processor is programmed to, in response to the at least one result, perform the act of requesting the user to provide information specifying a clinical relationship between the user and the at least one patient.

77. The agent of claim 53, wherein the computer system comprises a first computer, wherein the at least two software applications each comprises a user interface executing on the first computer, and wherein the at least one processor comprises at least one processor on the first computer programmed to provide a user interface for the agent on the first computer.

78. The agent of claim 77, wherein the computer system further comprises a second computer, and wherein the at least one processor further comprises at least one processor on the second computer that is programmed to perform at least some of the functionality of the agent and to communicate with the user interface for the agent.

79. The agent of claim 53, wherein one or more of the at least two software applications includes no native context-sharing functionality, and wherein the computer system comprises a component that enables the one or more software applications to share context with other of the at least two software applications.

80. The agent of claim 53, wherein the at least two software applications share context in accordance with a context-sharing protocol other than a CCOW standard.

* * * * *